US00PP24004P3

(12) United States Plant Patent
White et al.

(10) Patent No.: US PP24,004 P3
(45) Date of Patent: Oct. 29, 2013

(54) ***RHODANTHEMUM* PLANT NAMED 'CASABLANCA'**

(50) Latin Name: ***Rhodanthemum* hybrid**
Varietal Denomination: CASABLANCA

(76) Inventors: Anthony Robin White, Alresford (GB); Susan Barbara White, Alresford (GB)

( * ) Notice: Subject to any disclaimer, the term of this patent is extended or adjusted under 35 U.S.C. 154(b) by 262 days.

(21) Appl. No.: 13/136,117

(22) Filed: Jul. 22, 2011

(65) Prior Publication Data

US 2013/0025010 P1 Jan. 24, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Kent L Bell
(74) *Attorney, Agent, or Firm* — Cassandra Bright

(57) ABSTRACT

A new and distinct *Rhodanthemum* cultivar named 'CASABLANCA' is disclosed, characterized by compact plant growth, large flowers produced over a long period of time. Plants have a good tolerance for drought. The new variety is a *Rhodanthemum*, normally produced as an outdoor ornamental plant for containers or gardens.

1 Drawing Sheet

Latin name of the genus and species: *Rhodanthemum* hybrid.

Variety denomination: 'CASABLANCA'.

BACKGROUND OF THE INVENTION

The new cultivar was discovered as a result of a planned breeding program directed by the inventors, Anthony Robin White and Susan Barbara White, citizens of the United Kingdom. The seed parent is an unnamed, unpatented plant of *Rhodanthemum hosmariense* and the pollen parent is an unpatented variety of *Rhodanthemum* plant, of unknown species. The cross resulting in 'CASABLANCA' was made June 2004. The new variety was discovered during the Spring of 2008, by the inventors in a commercial nursery in Hampshire, United Kingdom.

Asexual reproduction of the new cultivar 'CASABLANCA' by vegetative cuttings was first performed in 2008, at a commercial nursery in Hampshire, United Kingdom. Multiple generations have since been produced and have shown that the unique features of this cultivar are stable and reproduced true to type in successive generations.

SUMMARY OF THE INVENTION

The cultivar 'CASABLANCA' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'CASABLANCA' These characteristics in combination distinguish 'CASABLANCA' as a new and distinct *Rhodanthemum* cultivar:

1. Compact growth habit.
2. Large flowers.

3. Long flowering period.
4. Good tolerance for drought.

PARENT COMPARISON

Plants of the new cultivar 'CASABLANCA' are similar to plants of the seed parent, a plant of *Rhodanthemum hosmariense* in most horticultural characteristics, however, plants of the new cultivar 'CASABLANCA' produce flowers over a 9 month period, whereas the seed parent produces flowers over a 4 to 5 month period. Additionally, the new variety produces foliage with a more silver-green appearance than the seed parent.

Plants of the new cultivar 'CASABLANCA' are similar to plants of the pollen parent in most horticultural characteristics, however, plants of the new cultivar 'CASABLANCA' are more compact in growth habit than the pollen parent. Additionally, the new variety has less foliage that is less silver-green than the pollen parent.

COMMERCIAL COMPARISON

'CASABLANCA' can be compared to the commercial variety *Rhodanthemum* 'African Eyes', unpatented. The two varieties are very similar in most horticultural characteristics, however, plants of 'CASABLANCA' produce larger flowers, and flowers over a longer period of time than 'African Eyes'. Additionally, plants of 'CASABLANCA' are more compact, produce foliage that is more silver-green, and have a better tolerance for drought.

BRIEF DESCRIPTION OF THE PHOTOGRAPH

The accompanying photograph in FIG. 1 illustrates in full color a typical plant of 'CASABLANCA' grown outdoors, in Hampshire, United Kingdom, in a commercial 15 cm container. Age of the plant photographed is approximately 9 months from a rooted cutting.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2001 except where general terms of ordinary dictionary significance are used. The following observations and measurements describe 'CASABLANCA' plants grown outdoors, during Spring months in Hampshire, United Kingdom. The growing temperature ranged from 10° C. to 25° C. daytime and 5° to 15° C. at night. No chemical treatments were given. Measurements and numerical values represent averages of typical plant types.

Botanical classification: *Rhodanthemum* hybrid 'CASABLANCA'.

PROPAGATION

Time to rooting: 18 to 21 days at approximately 21° C.
Time to produce a rooted cutting: 7 weeks.
Root description: Fine, fibrous, dense rooting habit.

PLANT

Growth habit: Hardy, upright, herbaceous perennial.
Height: Approximately 30 to 40 cm.
Plant spread: Approximately 30 to 40 cm.
Growth rate: Vigorous.
Branching characteristics: Free branching.
Length of lateral branches: Approximately 25 to 30 cm.
Diameter of lateral branches: Approximately 0.5 cm.
Quantity of lateral branches: Numerous.
Texture of lateral branches: Smooth, glabrous, strong.
Color of lateral branches: Near RHS Green N138 C.
Aspect: Approximately 40 to 45° angle from base of plant.
Internode length: Approximately 0.8 to 1 cm.
Number of leaves per lateral branch: Approximately 20 to 30.
Age of plant described: Approximately 9 months from a rooted cutting.

FOLIAGE

Leaf:
- *Arrangement.*—Alternate, simple.
- *Average length.*—Smallest apical leaves, approximately 1.5 to 2 cm. Largest basal leaves, approximately 3.5 to 4 cm.
- *Average width.*—Smallest apical leaves approximately 0.8 to 1 cm. Largest basal leaves, approximately 2.5 to 3 cm.
- *Shape of blade.*—Palmately lobed.
- *Apex.*—Acute to obtuse.
- *Base.*—Truncate.
- *Attachment.*—Sessile.
- *Margin.*—Entire.
- *Texture of top surface.*—Smooth, glabrous.
- *Texture of bottom surface.*—Smooth, glabrous.
- *Leaf internode length.*—Differs from branch to branch; from 2 to 6 cm.
- *Color.*—Young foliage upper side: Near RHS N 138A. Young foliage under side: Near RHS N 138A. Mature foliage upper side: Near RHS N 138A. Mature foliage under side: Near RHS N 138A.
- *Venation.*—Indistinguishable from foliage.

Petiole: Not present.

FLOWER

Bloom period: Naturally blooming: From early spring until late autumn; approximately 9 months.

Bud:
- *Bud shape.*—Spherical.
- *Bud length.*—Approximately 0.5 cm.
- *Bud diameter.*—Approximately 0.5 cm.
- *Bud color.*—Near RHS Green N 138A.

Inflorescence:
- *Form.*—Panicle, composed of composite type flowers.

Flower:
- *Diameter of entire flower.*—Approximately 2.5 to 3 cm.
- *Depth of flower.*—Approximately 0.5 to 0.8 cm (including receptacle).
- *Disc diameter.*—Approximately 0.8 cm.
- *Receptacle shape.*—Campanulate to cup shaped.
- *Receptacle height.*—Average 0.5 cm.
- *Receptacle diameter.*—Average 0.7 cm.
- *Quantity of inflorescences per lateral stem.*—10 to 15.
- *Quantity of open inflorescences and buds per plant.*—Average 50 to 60.
- *Longevity.*—20 days.
- *Rate of opening.*—5 to 7 days from bud to fully opened flower.
- *Persistent or self-cleaning.*—Persistent.

Ray florets:
- *Arrangement.*—Rotate composite inflorescence form with ray florets subtending and also developing at the apex of the receptacle.
- *Aspect/orientation.*—Funnel-shaped to horizontal, moving to outcurved.
- *Shape.*—Lanceolate.
- *Number of ray florets.*—Avg. 13.
- *Length.*—Approximately 0.8 to 1 cm.
- *Width.*—Approximately 0.5 cm.
- *Apex shape.*—Obtuse.
- *Base.*—Rounded.
- *Margin.*—Entire.
- *Texture.*—Smooth.

Color:
- *Ray florets.*—Upper surface at first opening: Near RHS 155C (white). Upper surface at maturity: Near RHS 155C (white). Upper surface at fading: No change. Under surface at first opening: Near RHS 155C (white). Under surface at maturity: Near RHS 155C (white). Under surface at fading: No change.
- *Disc florets.*—Number of Disc Florets: more than 200. Arrangement: Acropetally on disc. Length: Approximately 3 to 5 mm. Width: Approximately 8 mm. Shape: Tubular, lower ⅓ fused, upper ⅔ open. Margin: entire. Apex: acute. Base: Fused, acute. Texture: Smooth, glossy.

Color:
- *Disc florets.*—At first opening: Near RHS Greyed-Orange 166A. At maturity: Near RHS Greyed-Orange 165A. Fading: No change from mature stage.

Fragrance: No fragrance.

PHYLLARIES/INVOLUCAL BRACTS

- *Arrangement.*—Rotate.
- *Number.*—Approximately 1 to 2 per flower.
- *Length.*—Approximately 0.5 cm.

*Width.*—Approximately 0.5 cm.
*Shape.*—Palmately lobed, just like leafs/blades.
*Apex.*—Acute to obtuse.
*Base.*—Truncate.
*Margin.*—Entire.
*Texture.*—Smooth, glabrous.
*Color.*—Inside color near RHS N138A. Outside color near RHS N138A.

PEDUNCLE

*Length.*—Average 20 cm.
*Width.*—Average 0.3 cm.
*Texture.*—Pubescent.
*Color.*—Near RHS N 138D.

REPRODUCTIVE ORGANS

Disc florets:
*Androecium.*—Stamens per disc floret: Numerous and minute, quantity immeasurable. Filament length: Approximately 3 to 5 mm. Filament color: Near RHS Greyed-Orange 165B. Anther shape: oval. Anther length: About 3 mm. Anther color: Near RHS Greyed-Orange 164B. Pollen amount: Moderate to abundate. Pollen color: Near RHS Yellow-Orange 21 B.
*Gynoecium.*—Pistil length: Approximately 1 mm. Stigma shape: open. Stigma color: Near RHS Yellow-Orange 21C. Style length: About 1 to 2 mm. Style color: Near RHS Greyed-Orange 163B. Ovary color: Near RHS Green 138C.
Ray florets:
*Gynoecium.*—Present only disc florets.
*Androecium.*—Present only disc florets.

OTHER CHARACTERISTICS

Seeds and fruits: Not observed to date.
Disease/pest resistance: Neither resistance nor susceptibility to pathogens and pests common to *Rhodanthemum* have been observed.
Drought tolerance and temperature tolerance: Hardy perennial to −10° C. Upper temperature tolerance to at least 30° C. Good drought tolerance, established plants can tolerate infrequent summer waterings.

What is claimed is:

1. A new and distinct cultivar of *Rhodanthemum* plant named 'CASABLANCA' as herein illustrated and described.

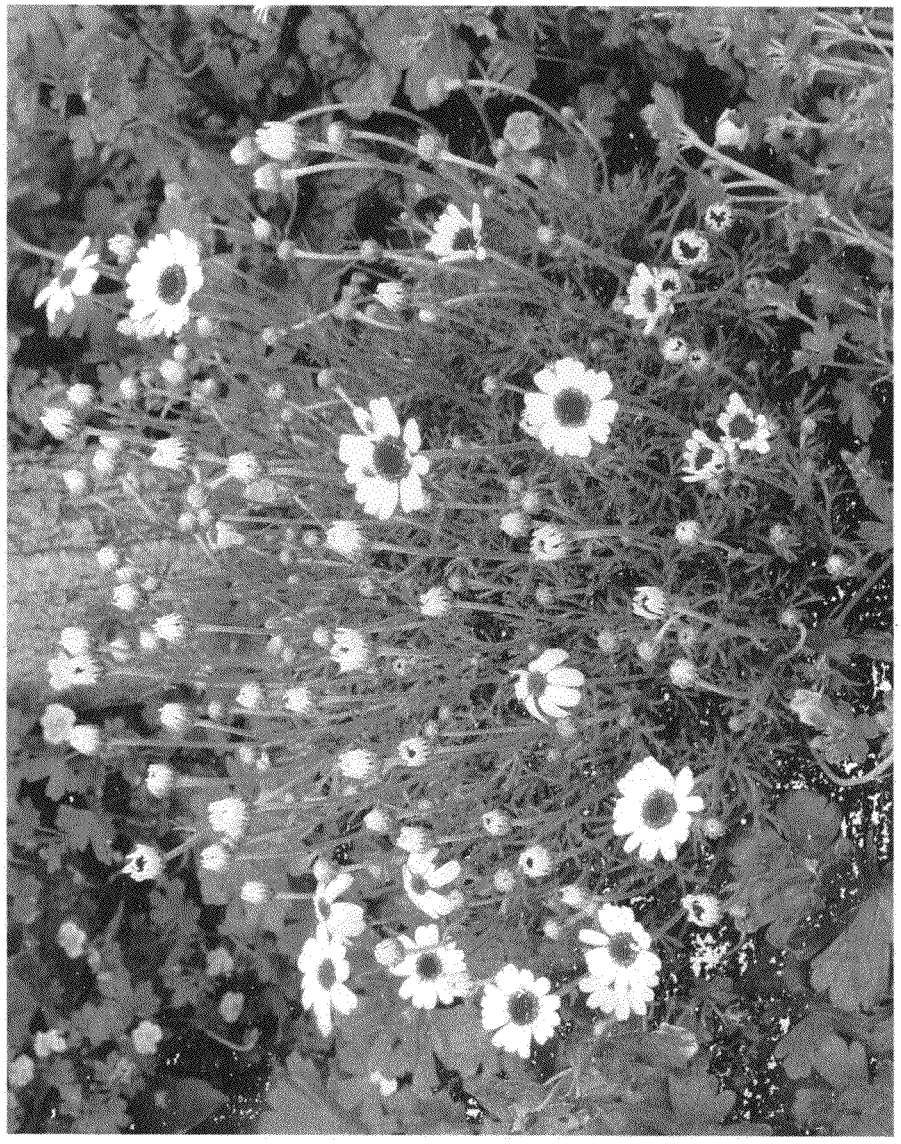

* * * * *